US 6,662,636 B2

(12) United States Patent
Shah et al.

(10) Patent No.: US 6,662,636 B2
(45) Date of Patent: Dec. 16, 2003

(54) METHOD OF REDUCING FOULING IN FILTERS FOR INDUSTRIAL WATER SYSTEM ANALYTICAL DEVICES

(75) Inventors: Jitendra T. Shah, Naperville, IL (US); Brian S. Johnson, Warrenville, IL (US)

(73) Assignee: Ondeo Nalco Company, Naperville, IL (US)

( * ) Notice: Subject to any disclaimer, the term of this patent is extended or adjusted under 35 U.S.C. 154(b) by 0 days.

(21) Appl. No.: 10/016,152

(22) Filed: Dec. 13, 2001

(65) Prior Publication Data

US 2003/0110842 A1 Jun. 19, 2003

(51) Int. Cl.[7] .............................................. B01D 35/22
(52) U.S. Cl. ................... 73/64.56; 73/863.24; 210/108; 210/343; 210/411; 210/427
(58) Field of Search ......................... 73/64.56, 863.24; 210/108, 295, 393, 411, 425, 427

(56) References Cited

U.S. PATENT DOCUMENTS

| | | | |
|---|---|---|---|
| 4,783,314 A | | 11/1988 | Hoots et al. |
| 4,966,711 A | | 10/1990 | Hoots et al. |
| 4,992,380 A | | 2/1991 | Moriarty et al. |
| 5,006,311 A | | 4/1991 | Hoots et al. |
| 5,013,457 A | * | 5/1991 | Mims ......................... 210/741 |
| 5,043,406 A | | 8/1991 | Fong |
| 5,171,450 A | | 12/1992 | Hoots |
| 5,278,074 A | | 1/1994 | Rao et al. |
| 5,354,466 A | * | 10/1994 | Yunoki ................... 210/321.69 |
| 5,378,784 A | | 1/1995 | Fong et al. |
| 5,389,548 A | | 2/1995 | Hoots et al. |
| 5,411,889 A | | 5/1995 | Hoots et al. |
| 5,413,719 A | | 5/1995 | Sivakumar et al. |
| 5,645,799 A | | 7/1997 | Shah et al. |
| 5,658,798 A | | 8/1997 | Bertin et al. |
| 5,702,684 A | | 12/1997 | McCoy et al. |
| 5,714,387 A | | 2/1998 | Fowee et al. |
| 5,736,405 A | | 4/1998 | Alfano et al. |
| 5,893,973 A | * | 4/1999 | Antoun ....................... 210/411 |
| 5,919,707 A | | 7/1999 | Banks et al. |
| 5,958,788 A | | 9/1999 | Johnson et al. |
| 5,986,030 A | | 11/1999 | Murray et al. |

* cited by examiner

Primary Examiner—Daniel S. Larkin
(74) Attorney, Agent, or Firm—Margaret M. Brumm; Thomas M. Breininger

(57) ABSTRACT

The invention is in a method of analyzing the water of an industrial water system wherein an analytical device is used to measure some parameter capable of being measured in the water of said industrial water system, the improvement involving using a water movement device that is capable of moving a sample of water into the sample chamber of said analytical device and is also capable of moving the same sample of water back out of said analytical device in a manner such that the filters present in the piping of said industrial water system are back flushed out every time the water movement device moves a sample of water in and out of said analytical device. Optionally an air sparge is used to enhance the cleaning of the filters.

16 Claims, No Drawings

METHOD OF REDUCING FOULING IN FILTERS FOR INDUSTRIAL WATER SYSTEM ANALYTICAL DEVICES

FIELD OF THE INVENTION

This invention relates to an improved method of reducing fouling in filters for industrial water system analytical devices.

BACKGROUND OF THE INVENTION

In the method of operation of many industrial water systems it is routine procedure to have analytical devices present to analyze parameters of interest concerning the water in the industrial water system. Some of these analytical devices are simple devices, such as thermometers, pH meters, turbidimeters, and conductivity probes, which are measurement devices that involve placing a sensing mechanism of the analytical device directly into the water of the industrial water system.

Other analytical devices are more complicated and require that the water in the industrial water system actually flow through a sample chamber of the analytical device. These more complicated devices include such equipment as streaming current detectors, particle counters, particle sizers, and fluorometers. A streaming current detector is a device capable of measuring absorbable charge in water. A particle counter for water treatment and monitoring directly counts individual particles and tallies according to the individual particle size. The two commonly used methods are light extinction and light scattering. Light extinction directly measures the amount of light obfuscated; the more light blocked, the larger the particle. Assuming spherical particle shape, the light obfuscation is compared to a calibration curve and the particle size calculated and this 'count' is tallied in the appropriate size bin. After counting thousands of particles, a particle size distribution is developed. This is considered a direct method of obtaining the particle size distribution.

A particle sizer measures some metric, such as sound attenuation, and analytically calculates the particle size distribution. This is considered an indirect method of obtaining the particle size distribution. A fluorometer is a device capable of measuring one or more fluorescent signals of one or more fluorescent moieties present in the water. This type of analysis is useful in industrial water systems wherein a fluorescent moiety is present and functioning as a tracer of either the water in the industrial water system or as a tracer of a treatment product or as a fluorescently-tagged moiety that acts as some sort of treatment product.

It has been found that when a sample of water from an industrial water system is moved through an analytical device that it is desirable to filter the water prior to its entering the analytical device. The purpose of filtering is to remove contaminants and other material present in the water that could foul the sample chamber of the analytical device. Filters suitable for this purpose are known to people of ordinary skill in the art of industrial water systems and are commercially available. A known problem with these filters is that during continuous operation they frequently become so plugged with material present in the industrial water system that it is necessary to clean or replace them at regular intervals. Cleaning filters in the piping of an industrial water systems typically involves removing the filter, cleaning or replacing the filter, and then reinstalling the filter in the industrial water system. This type of cleaning is highly labor intensive and time consuming. Additionally, the time interval after clogging and before filter cleaning or replacement, negatively impacts on system performance.

Therefore, it would be desirable to find a way to reduce the amount of fouling present in the filters of an analytical device in an industrial water system.

SUMMARY OF THE INVENTION

In a method of analyzing the water of an industrial water system wherein an analytical device is used to measure some parameter capable of being measured in the water of said industrial water system, the improvement comprising using a water movement device that is capable of moving a sample of water into the sample chamber of said analytical device and is also capable of moving the same sample of water back out of said analytical device in a manner such that the filters present in the piping of said industrial water system are back flushed out every time the water movement device moves a sample of water in and out of said analytical device.

DESCRIPTION OF THE PREFERRED EMBODIMENTS

The instant claimed invention is in a method of analyzing the water of an industrial water system wherein an analytical device is used to measure some parameter capable of being measured in the water of said industrial water system, the improvement comprising using a water movement device that is capable of moving a sample of water into the sample chamber of said analytical device and is also capable of moving the same sample of water back out of said analytical device in a manner such that the filters present in the piping of said industrial water system are back flushed out every time the water movement device moves a sample of water in and out of said analytical device.

Industrial water systems include cooling tower water systems (including open recirculating, closed, and once-through cooling tower water systems); petroleum wells, downhole formations, geothermal wells, and other oil field applications; boilers and boiler water systems; mineral process waters including mineral washing, flotation, and benefaction; pulp mill process streams, pulp mill digesters, washers, bleach plants, and white water systems; black liquor evaporators in the pulp industry; gas scrubbers and air washers; continuous casting processes in the metallurgical industry; air conditioning and refrigeration systems; industrial and petroleum process water; indirect contact cooling and heating water, such as pasteurization water; water reclamation and purification systems; membrane separation processes, membrane filtration water systems; clarifiers, dissolved air flotation clarifiers, aeration basins, oil-in-water systems, water-in-oil systems, oil separations, sludge dewatering, food processing streams; waste treatment systems as well as in liquid-solid applications, municipal sewage treatment systems and industrial or municipal water systems.

Such waters contain solids (or oils) and liquids and are often once-through systems where the waste water is not recirculated. The preferred industrial water system for the method of the instant claimed invention are those water systems that have a significant amount of solids present in the water. These systems include waste treatment systems, municipal sewage treatment systems, and pulp mill process streams.

Analytical devices suitable for use in this method are those analytical devices that have a sample chamber that must be filled with a sample of water. The water in the sample is then analyzed by the analytical device. The sample chamber of many analytical devices is a "fill-up and then empty-out" chamber or the sample chamber can alternatively be configured such that water is continuously moved through the sample chamber.

Typically, the sample of water remains in the sample chamber long enough for the analytical device to analyze the parameter it is designed to analyze. Many times there is a waiting period before the analytical device takes the reading because of the need to wait for the sample to equilibrate. For example, typically with a fluorometer it is necessary to wait long enough for any air bubbles in the sample to dissipate, otherwise the air bubbles could interfere with the analytical device analyzing the water.

For a fluorometer, the typical time period within the sample chamber for the water is from about 5 seconds to 10 minutes, preferably from about 30 seconds to about 7 minutes, and most preferably about 5 minutes.

Analytical devices suitable for use with the instant claimed invention include turbidimeters, streaming current detectors, particle counters, particle sizers, conductivity meters, and fluorometers. The preferred analytical device is a fluorometer.

Fluorometers suitable for use in the instant claimed invention are available from ONDEO Nalco Company, ONDEO Nalco Center, Naperville, Ill. 60563 (630) 305–1000 (hereinafter "NALCO"). The preferred fluorometer is a TRASAR® 3000 fluorometer.

Whatever fluorometer is chosen, the fluorometer must be configured such that the water is sampled, measured, and discharged to the same point. This can be done by simply configuring the fluorometer such that the inlet pipe to the fluorometer sample chamber is the same as the exit pipe and the filter is positioned in the inlet/exit pipe. The reason for the filter is that the inlet to the fluorometer sample chamber has a filter over it to filter out suspended solids so the sample chamber is not contaminated by those solids. It is this filter that tends to foul most often.

The parameter capable of being measured is dependent upon the analytical device. If a fluorometer is used, then the parameter capable of being measured is the fluorescent signal of some fluorescent moiety present in the water of the industrial water system.

If the fluorometer is the analytical device chosen then it is possible to use the fluorescent signal of a fluorescent moiety present in a treatment product. The preferred fluorescent moieties are those known to people of ordinary skill in the art of fluorescent tracers. See U.S. Pat. Nos. 4,783,314; 4,966,711; 4,992,380; 5,006,311; 5,043,406; 5,171,450; 5,278,074; 5,378,784; 5,389,548; 5,411,889; 5,413,719; 5,645,799; 5,658,798; 5,702,684; 5,714,387; 5,736,405; 5,919,707; 5,958,788; and 5,986,030, all of which are incorporated by reference.

The water movement device is typically a pump, configured such that its intake and exit piping are the same pipe. This is contrary to the normal configuration for a pump, so creating a pump like this involves reorienting the piping such that the intake and exit piping are the same. The preferred pump is a piston pump with the foot valve removed such that the intake and exit for the pump are the same pipe. A piston pump suitable for use in this method is available from Blackhawk Pumps and Controls, 21W159 Hill Avenue, Glen Ellyn, Ill. 60137, telephone number (630) 469–4916. Piston pumps typically are manufactured with a foot valve installed, so in order to work in the method of the instant claimed invention, the foot valve must be removed.

With the pump configured such that its inlet and exit are the same, the water sample moved by the pump is first forced through a filter into the sample chamber of the analytical device. The water remains in the sample chamber long enough for the analytical device to complete the analysis. After the water has been analyzed, the water sample is removed from the sample chamber on the back stroke of the pump. The removal of the water sample from the sample chamber forces the water back through the filter and acts to automatically clean the filter. This automatic filter cleaning action means that it is not necessary to manually clean the filter.

Optionally, an air sparge can be used to enhance the evacuation of the sample chamber and to also enhance removal of particulates from the filter on the inlet leading into the analytical device. The use of a commercially available standard air sparge activated by a commercially available solenoid to enhance filter cleaning is a preferred configuration to conduct the method of the instant claimed invention.

The following examples are presented to describe preferred embodiments and utilities of the invention and are not meant to limit the invention unless otherwise stated in the claims appended hereto.

EXAMPLES

Example 1

Plant 1 is a wastewater plant, located in Illinois and has a wastewater flow of approximately 24 million gallons per day (hereinafter "MGD"). The plant is a waste activated process and aerobically digests the thickened sludge (about 1% solids by weight) and later dewaters the sludge through two centrifuges.

The centrifuges are from Humboldt and have a design flow of 350 gallons per minute (hereinafter "gpm") with feed solids typically 1 to 1.5 percent.

Nalco 00MU085 is a commercially available product of Nalco. Nalco 00MU085 contains a polyacrylamide based flocculant terpolymer and a fluorescent moiety which is pyrene tetrasulfonic acid. Plant 1 schedules a trial of Nalco 00MU085 for use as a sludge dewatering polymer to replace the treatment polymer they are currently using.

The trial is begun using a TRASAR® 3000 fluorometer configured such that it is possible to detect the fluorescent signal of the pyrene tetrasulfonic acid. The sample chamber of the TRASART® 3000 operates on a enter, pass-through, and then out configuration, wherein the sample water entering the sample chamber leaves without being forced back through the inlet to the sample chamber.

The trial begins and it is possible to detect the fluorescent signal of the pyrene tetrasulfonic acid using the TRASAR® 3000 fluorometer. A control computer uses the fluorescent signal of the pyrene tetrasulfonic acid to control the feedrate of the pump that is pumping Nalco 00MU085 in the water of Plant 1. During the first day of the trial, it was found that the filter to the fluorometer was fouling due to the high level of particulate matter in the sludge that is to be dewatered. It was necessary to have the fluorometer shut down so that the filter could be pulled, cleaned, and replaced. This meant that control of the Nalco 00MU085 could not be continuous, as is recommended.

In order to be able to conduct the trial with continuous control, the existing peristaltic pump is replaced with a piston pump from Blackwell. The Blackwell piston pump is configured such that the inlet piping (plumbing) and outlet piping (plumbing) are the same. This is done by buying a commercial Blackhawk piston pump and changing its configuration by removing the foot valve. {If the foot valve is left in place it prevents water from being pushed out the inlet plumbing.} After the foot valve is removed the piston pump becomes a device capable of moving water "in-and-out" of the sample chamber of the TRASAR® 3000 fluorometer. When configured in this set-up water flows through the filter and into the inlet into the fluorometer sample chamber. The water is pumped out of the fluorometer sample chamber through the same orifice in the opposite direction. The piston pump is inserted in the process piping such that it acts to force water into the sample chamber of a fluorometer.

A TRASAR® 3000 fluorometer is used and configured in the normal way, except that the reference wavelength intensity is always assumed to be unity (meaning no excitation intensity compensation is used). This is done by replacing the factory installed ROM chip with different, non-standard firmware programming. The excitation wavelength is set at 365 nm and the emission wavelength is set at 400 nm in order to detect the fluorescent signal of the PTSA present in the polymer flocculent.

Analysis of the data shows that when the plant is running using manual (non-fluorometric control) control the plant is running at 9.75 gpm inverted polymer output, then with the activation of automatic control based on using the traced flocculant polymer, the feedrate of traced polymer drops to 5.69 gpm within 2 hours. After 3.5 hours, the feedrate of traced polymer equilibrates at 7.31 gpm. In this time, a feedrate reduction of 2.44 gpm (25% reduction) is realized. This means that it is possible to feed just the right amount of sludge dewatering aid without feeding too much (wasting polymer and costing money that need not be spent) or feeding too little (having the sludge not being properly treated).

Using the method of the instant claimed invention makes it possible to run Plant 1 while reducing the amount of time required in cleaning and maintaining the filters in the piping leading to the fluorometer sample chamber.

Example 2

Plant 2 is a different wastewater plant also located in Illinois and has a wastewater flow of approximately 22 MGD. The plant uses a waste activated process and anaerobically digests the thickened sludge. Digested sludge is also dewatered through Humboldt centrifuges with a design flow of 200 gpm. Here the sludge feed solids typically are 2 to 3 weight percent.

Nalco 00MU086 is a commercially available product of Nalco. Nalco 00MU086 contains a polyacrylamide based flocculant copolymer and a fluorescent moiety which is pyrene tetrasulfonic acid. Plant 2 schedules a trial of Nalco 00MU086 for use as a sludge dewatering polymer to replace the treatment polymer they are currently using.

The trial is begun using a TRASAR® 3000 fluorometer configured such that it is possible to detect the fluorescent signal of the pyrene tetrasulfonic acid. The sample chamber of the TRASAR® 3000 is configured the same as in Example 1.

Based on the knowledge gained in the trial at Plant 1, the pump used to move water into the sample chamber of the fluorometer is a piston pump from Blackwell that has previously had the foot valve removed.

A TRASAR® 3000 fluorometer is used and configured the same as described in the trial at Plant 1.

In conducting the trial, some forty minutes after the trial begins, the control is switched from manual to automated control. Using the fluorescent signal of the PTSA, it is determined that an excess of polymer (an overdose situation) is being fed. With manual operation the polymer feedrate is 51 lbs. per dry ton of solids and after 6.5 hours of acceptable operation using the fluorescent signal of the PTSA, the system automatically reduces the feed of Nalco 00MU086 to 38 lbs. per dry ton.

The industrial water system is then put back on manual control. The next day, a slight underdose of 44 lbs. per dry ton is identified when control of Plant 2 is changed back to automated control. Within the first 7.5-hour time period, polymer usage is raised to 47 lbs. per dry ton, then the system is placed back on manual control for overnight operation. This dose is found to be acceptable during overnight operations and then the system is placed on automated control, which produces acceptable results.

As was the case with the trial conducted in Plant 1, running the industrial water system of Plant 2 in the manner indicated allows automatic control of treatment polymer feed using the fluorescent signal of the fluorescent moiety present in the treatment product.

Changes can be made in the composition, operation, and arrangement of the method of the present invention described herein without departing from the concept and scope of the invention as defined in the following claims:

What is claimed is:

1. In a method of analyzing the water of an industrial water system wherein an analytical device is used to measure some parameter capable of being measured in the water of said industrial water system, wherein a filter is present in the piping of said industrial water system, and wherein said filter is located either prior to the inlet pipe or in the inlet pipe of said analytical device, the improvement comprising using a water movement device that is capable of moving a sample of water through said filter into the sample chamber of said analytical device and is also capable of moving the same sample of water back out of said analytical device in a manner such that the filters present in the piping of said industrial water system is back flushed out every time the water movement device moves a sample of water in and out of said analytical device.

2. The method of claim 1 in which said analytical device is a fluorometer.

3. The method of claim 1 in which said analytical device is a streaming current detector.

4. The method of claim 1 in which said analytical device is a particle counter or a particle sizer.

5. The method of claim 2 in which said parameter capable of being measured is the fluorescent signal of a fluorescent moiety present in the water.

6. The method of claim 3 in which said parameter capable of being measured is the measured charge in the water.

7. The method of claim 4 in which said measured parameter is the number of particles present in the water or the size of the particles measured in the water.

8. The method of claim 1 in which said water movement device is a pump.

9. The method of claim 8 in which said pump is a piston pump.

10. The method of claim 9 in which said piston pump has had the foot valve removed.

11. The method of claim 1 wherein an air sparge is used to enhance filter cleaning.

12. The method of claim 1 in which said industrial water system is a sludge dewatering system.

13. The method of claim 1 in which said industrial water system is a pulp mill process stream.

14. The method of claim 1 in which said industrial water system is a municipal sewage treatment system.

15. The method of claim 1 in which said industrial water system is a boiler.

16. The method of claim 1 in which said industrial water system is a cooling tower water system.

* * * * *